US012742776B2

(12) United States Patent
Karlsson

(10) Patent No.: US 12,742,776 B2
(45) Date of Patent: Sep. 22, 2026

(54) METHOD AND SYSTEM FOR EVALUATION OF AN INTERACTION BETWEEN AN ANALYTE AND A LIGAND USING A BIOSENSOR

(71) Applicant: CYTIVA SWEDEN AB, Uppsala (SE)

(72) Inventor: Olof Karlsson, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 1210 days.

(21) Appl. No.: 17/577,138

(22) Filed: Jan. 17, 2022

(65) Prior Publication Data

US 2022/0137039 A1 May 5, 2022

Related U.S. Application Data

(63) Continuation of application No. 15/760,754, filed as application No. PCT/EP2016/072618 on Sep. 22, 2016, now Pat. No. 11,255,851.

(30) Foreign Application Priority Data

Sep. 25, 2015 (GB) ..................................... 1516992

(51) Int. Cl.
*G01N 33/543* (2006.01)
*G01N 33/557* (2006.01)
(Continued)

(52) U.S. Cl.
CPC . *G01N 33/54366* (2013.01); *G01N 33/54373* (2013.01); *G01N 33/557* (2013.01); *G01N 2021/4126* (2013.01); *G01N 21/553* (2013.01)

(58) Field of Classification Search
CPC ......... G01N 33/5304; G01N 33/54366; G01N 33/54373; G01N 33/557; G01N 21/553;
(Continued)

(56) References Cited

U.S. PATENT DOCUMENTS 5,242,828 A 9/1993 Bergstrom et al.
5,313,264 A 5/1994 Ivarsson et al.
(Continued)

FOREIGN PATENT DOCUMENTS

CN 102656464 A 9/2012
CN 102667448 A 9/2012
(Continued)

OTHER PUBLICATIONS

BioRad Proteon XPR36 manual, 2011.
(Continued)

*Primary Examiner* — Christopher L Chin
(74) *Attorney, Agent, or Firm* — CM Law; Jeff B. Vockrodt

(57) ABSTRACT

The present invention relates to a method for evaluation of an interaction between an analyte in a fluid sample and a ligand immobilized on a sensor surface of a biosensor, comprising the steps of providing (101) a plurality of fluid samples, each containing known concentrations of analyte providing (102) a plurality of needles and a plurality of sensor surfaces or detection spots, at least some of the sensor surfaces or detection spots having a known amount of ligand immobilized thereon, and each needle being configured to inject a fluid sample to a sensor surface or detection spots dividing (103) said plurality of fluid samples into at least two groups injecting (104) the fluid samples of a first of said groups to the sensor surfaces or detection spots by means of the needles to permit association of the analyte to the ligand monitoring (104) each sensor surface or detection spot and collecting binding data, and (Continued)

repeating (105) the steps of injecting fluid samples and monitoring detection spots and collecting binding data for each group of fluid samples, wherein the steps above are performed sequentially, without intermediate regeneration or renewal of the immobilized ligand.

The invention also relates to a biosensor system for evaluation of an interaction between an analyte in a fluid sample and a ligand immobilized on a sensor surface, to software for performing the steps of the method and to a computer readable medium for storing said software.

9 Claims, 4 Drawing Sheets

(51) Int. Cl.
*G01N 21/41* (2006.01)
*G01N 21/552* (2014.01)

(58) Field of Classification Search
CPC ............ G01N 2021/4126; G01N 33/48; B01L 3/5025; B01L 2300/0829
USPC ........... 422/407, 552, 553, 82.11; 435/288.7, 435/808; 436/164, 517, 524, 527, 809
See application file for complete search history.

(56) References Cited

U.S. PATENT DOCUMENTS 5,436,161 A 7/1995 Bergstrom et al.
5,492,840 A 2/1996 Malmqvist et al.
5,753,518 A * 5/1998 Karlsson .......... G01N 33/54373 436/805
11,255,851 B2 * 2/2022 Karlsson .......... G01N 33/54373
2004/0002167 A1 1/2004 Andersson et al.
2005/0014179 A1 1/2005 Karlsson et al.
2005/0074903 A1 4/2005 Amano
2007/0231880 A1 10/2007 Chang-Yen et al.
2012/0244637 A1 9/2012 Karlsson
2012/0264233 A1 10/2012 Jansson
2013/0065251 A1 3/2013 Karlsson et al.

FOREIGN PATENT DOCUMENTS

WO 2003044217 A2 5/2003
WO 2004109284 A1 12/2004
WO 2013058879 A2 4/2013

OTHER PUBLICATIONS

Bravman (2008) Cell Molec BioEn vol. 1, p. 216-228.

Chinese Office Action mailed Apr. 1, 2020.

Domnanich, Patrick et al., “Protein Microarray for the Analysis of Human Melanoma Biomarkers,” Sensors and Acutators B: Chemical: International Journal Devoted to Research and Development of Physical and Chemical Transducers, vol. 139, No. 1, Jun. 5, 2008, pp. 2-8.

EP Office Action for corresponding EP application No. 16770493.1 mailed Feb. 13, 2019, 5 pages.

GB Search Report for corresponding GB application No. GB1516992.3 mailed Jun. 23, 2016, 4 pages.

International Search Report for corresponding PCT application No. PCT/EP20161072618 mailed Dec. 7, 2016, 14 pages.

Mendoza, G. et a., “High-Throughput Microarray-Based Enzyme-Linked Immunosorbent Assay (Elisa),” Biotechniques Rapid Dispatches, Informa Healthcare, US, vol. 27, No. 4, Oct. 1, 1999, pp. 778, 780, 782-786, 788.

Nickerson, D A et al., “Automated DNA Diagnostics Using an Elisa-Based Oligonucleotide Ligation Assay,” Proceedings of the National Academy of Sciences of the United States of America, national Academy of Sciences, US, vol. 87, No. 22, Nov. 1, 1990, pp. 8923-8927.

Office Action received in Chinese Application No. 202311255858.8 dated May 20, 2026, with translation, 17 pages.

* cited by examiner

METHOD AND SYSTEM FOR EVALUATION OF AN INTERACTION BETWEEN AN ANALYTE AND A LIGAND USING A BIOSENSOR

CROSS-REFERENCE TO RELATED APPLICATIONS

This application is a continuation of U.S. patent application Ser. No. 15/760,754, filed Mar. 16, 2018, now U.S. Pat. No. 11,255,851, which is a filing under 35 U.S.C. 371 of international application number PCT/EP2016/072618, filed Sep. 22, 2016, which claims priority to Great Britain application number GB1516992.3, filed Sep. 25, 2015, the entire disclosure each of which is hereby incorporated by reference.

TECHNICAL FIELD

The present invention relates to a method and system for evaluation of an interaction between an analyte in a fluid sample and a ligand immobilized on a sensor surface of a biosensor, and to software for performing the steps of the method and a computer readable medium for storing said software

BACKGROUND

Analytical sensor systems that can monitor interactions between molecules, such as biomolecules, in real time are gaining increasing interest. These systems are often based on optical biosensors and usually referred to as interaction analysis sensors or biospecific interaction analysis sensors. A representative such biosensor system is the BIACORE® instrumentation sold by GE Healthcare, which uses surface plasmon resonance (SPR) for detecting interactions between molecules in a sample and molecular structures immobilized on a sensing surface. As sample is passed over the sensor surface, the progress of binding directly reflects the rate at which the interaction occurs. Injection of sample is followed by a buffer flow during which the detector response reflects the rate of dissociation of the complex on the surface. A typical output from the BIACORE® system is a graph or curve describing the progress of the molecular interaction with time, including an association phase part and a dissociation phase part. This graph or curve, which is usually displayed on a computer screen, is often referred to as a binding curve or "sensorgram".

With the BIACORE® system (and analogous sensor systems) it is thus possible to determine a plurality of interaction parameters for the molecules used as ligand and analyte. These parameters include kinetic rate constants for binding (association) and dissociation in the molecular interaction as well as the affinity for the surface interaction. The association rate constant ($k_a$) and the dissociation rate constant ($k_d$) can be obtained by fitting the resulting kinetic data for a number of different sample analyte concentrations to mathematical descriptions of interaction models in the form of differential equations. The affinity (expressed as the affinity constant $K_A$ or the dissociation constant $K_D$) can be calculated from the association and dissociation rate constants.

Before the biosensor system can be used to analyze an interaction, however, it is often necessary to determine properties of the molecules in order to increase the quality of the results. These properties are the analyte concentration interval suitable for achieving the desired binding curves and the amount of ligand to be mounted on the sensor plate, among others. If the concentration of analyte is too low or too high, the resulting binding curves are difficult to analyze and may not yield the correct determination of the interaction parameters. Similarly, if the amount of ligand is too small so will the sensor response be, and if the amount of ligand is too high it may be difficult for the analyte to bind to it as intended. To overcome these problems, calculations and analyses are performed beforehand, often taking several days or weeks in order to determine the operational parameters most likely to provide satisfactory results. A dilution series comprising fluid samples with different concentrations of analyte within an interval is generally used to create a plurality of binding curves in the hope that at least some of them can be used.

These preparations are generally time consuming and so is the acquiring of binding curves for every sample in a dilution series, since a regeneration of the sensor plate is often required between samples. Scouting for useful regeneration conditions might in itself be a process that takes hours or even weeks.

There is therefore a need for improvements within this field, both with regard to the preparation needed before using the biosensor and to the time consumption of the subsequent experiments.

SUMMARY OF THE INVENTION

The object of the invention is to provide a new method and biosensor system for evaluation of an interaction between an analyte in a fluid sample and a ligand immobilized on a sensor surface of a biosensor, which method and biosensor system overcomes one or more drawbacks of the prior art. This is achieved by the method and biosensor system as defined in the independent claims.

Thanks to the invention, a large number of interactions between analyte and ligand can be observed, stored, analyzed and displayed, giving good results without requiring calculations and experiments beforehand. Furthermore, thanks to the analysis being performed sequentially, without intermediate regeneration or renewal of the immobilized ligand, the interactions take place during a shorter time than previously known methods and system, saving further time and effort while still acquiring good results.

The fluid samples containing analyte can be a dilution series where each sample has a concentration of analyte that differs from all other samples, to maximize the number of different interactions performed, or can alternatively be a dilution series where at least two samples has the same concentration to further increase the quality of results and assist in eliminating contaminations, temporary disturbances or other faults.

The binding data obtained can be combined to form binding curves, one for each needle of the biosensor system, and are preferably displayed together in a single graph, to give a user a quick overview of the results and facilitate the identification of binding curves unsuitable for further analysis. Such binding curves may be removed by a user after visual inspection or by software configured to use some criteria, such as a total response value or a predetermined value for the increase in response over the entire curve, among others. After removal of such binding curves, the resulting binding curves are preferably displayed together and used for further analyses to obtain kinetic parameters or other data regarding the interaction between analyte and ligand.

The amount of ligand immobilized on the sensor surfaces of the biosensor system may vary, allowing for determination of steric effects and mass transport properties.

Many additional benefits of the invention will become readily apparent to the person skilled in the art in view of the detailed description below.

DRAWINGS

The invention will now be described in more detail with reference to the appended drawings, wherein.

Figure 3:
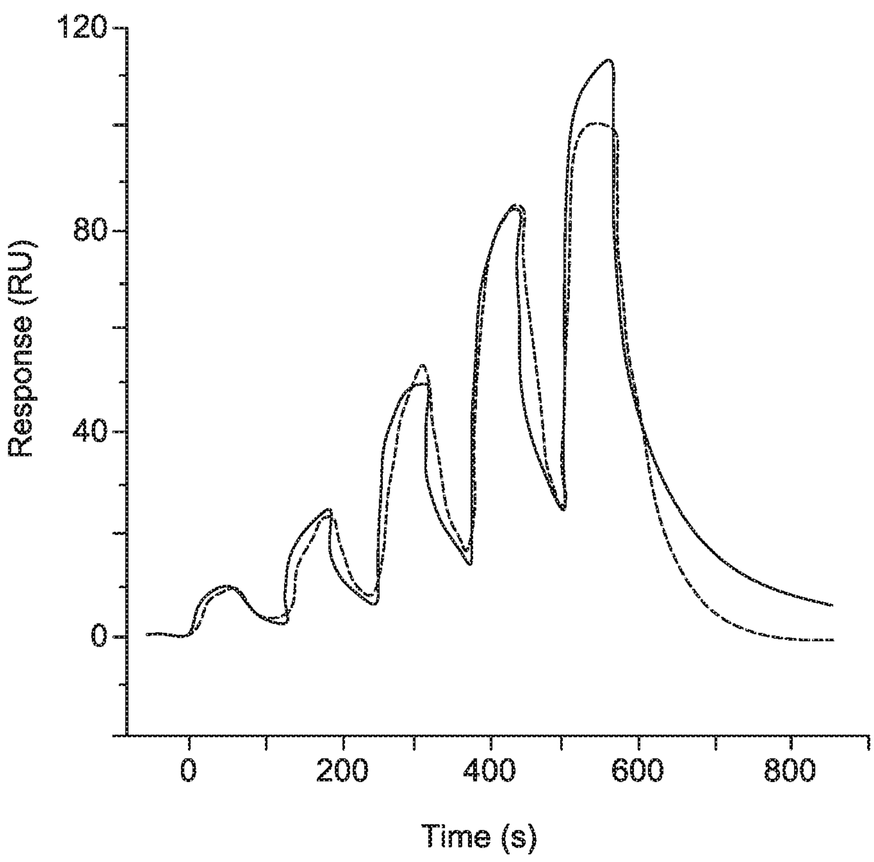
Figure 4:
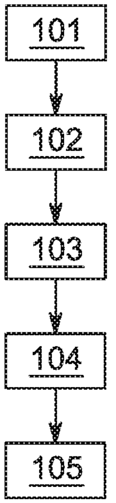
Figure 5:
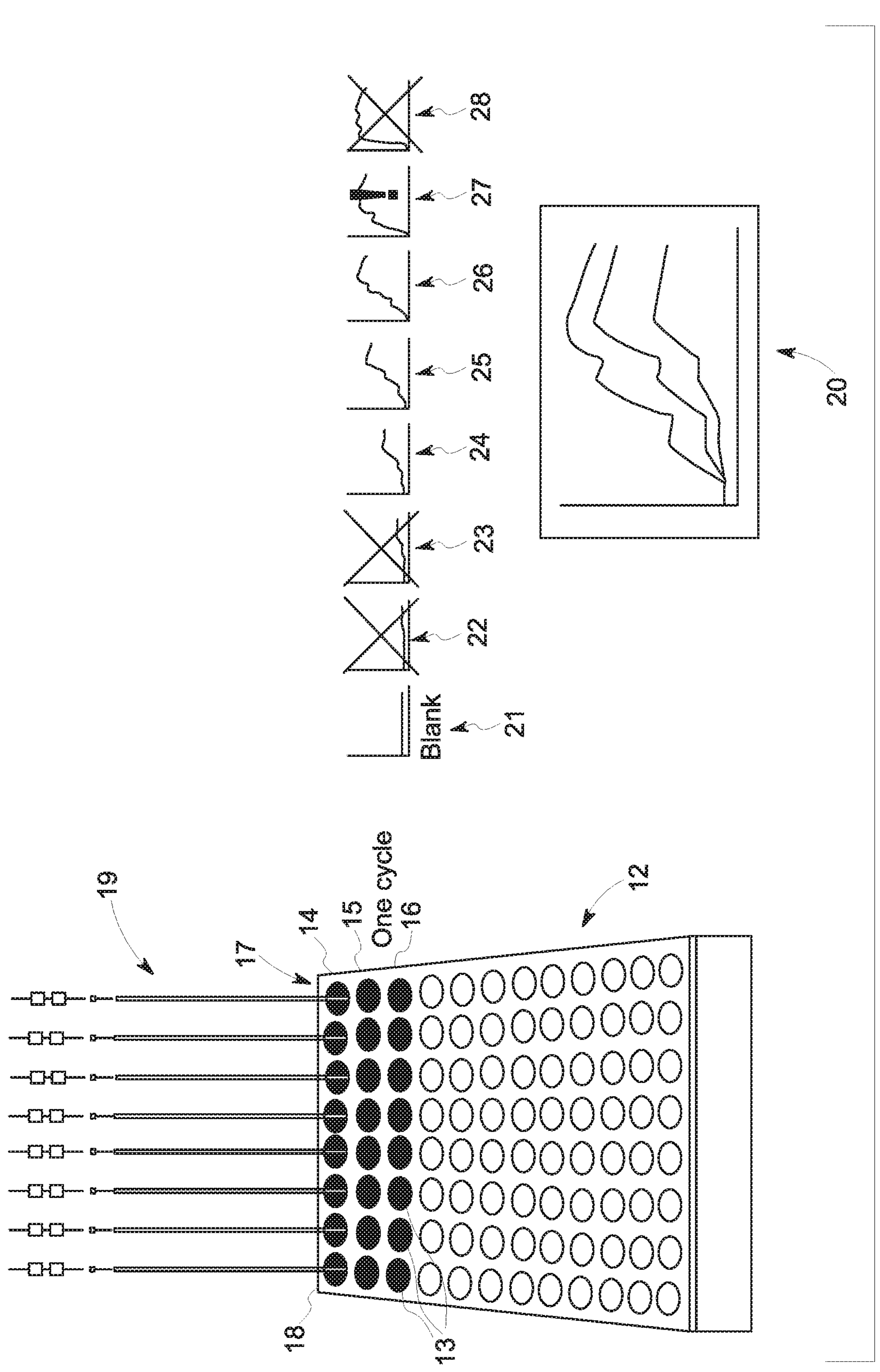
Figures 6, 7:
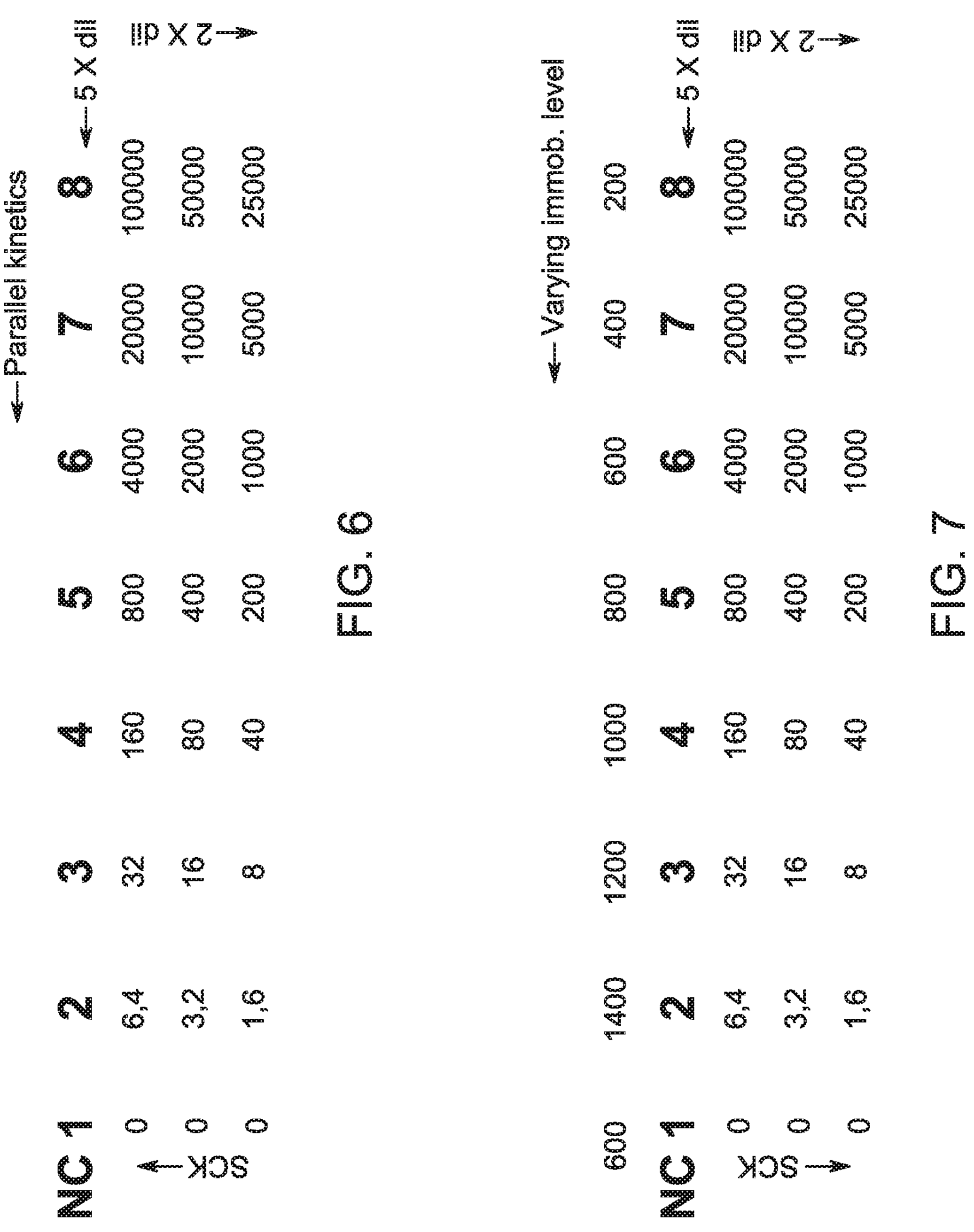

FIG. 3 discloses a single cycle analysis where a plurality of fluid samples containing analyte at different concentrations are injected without regeneration;

FIG. 4 shows the steps of the method according to a preferred embodiment of the invention;

FIG. 5 shows a plate with wells for holding fluid samples, part of a biosensor system with parallel needles and resulting graphs describing interaction between ligand and analyte;

FIG. 6 shows a dilution series suitable for use with the invention; and

FIG. 7 shows a dilution series with varying degrees of immobilized ligand for each column.

DETAILED DESCRIPTION

As mentioned above, the present invention relates to a method and a biosensor system for evaluation of an interaction between an analyte in a fluid sample and a ligand immobilized on a sensor surface of a biosensor.

Typically, the experimental binding data is obtained by sensor-based technology, which studies the molecular interactions and presents the results in real time as the interactions progress. Before describing the present invention in more detail, however, the general context in which the invention is intended to be used will be described.

Unless defined otherwise, all technical and scientific terms used herein have the same meaning as commonly understood by a person skilled in the art related to this invention. Also, the singular forms "a", "an", and "the" are meant to include plural reference unless it is stated otherwise.

All publications, patent applications, patents, and other references mentioned herein are incorporated by reference in their entirety.

Chemical sensors or biosensors are typically based on label-free techniques, detecting a change in a property of a sensor surface, such as e.g. mass, refractive index, or thickness for the immobilized layer, but there are also sensors relying on some kind of labelling. Typical sensor detection techniques include, but are not limited to, mass detection methods, such as optical, thermo-optical and piezoelectric or acoustic wave methods (including e.g. surface acoustic wave (SAW) and quartz crystal microbalance (QCM) methods), and electrochemical methods, such as potentiometric, conductometric, amperometric and capacitance/impedance methods. With regard to optical detection methods, representative methods include those that detect mass surface concentration, such as reflection-optical methods, including both external and internal reflection methods, which are angle, wavelength, polarization, or phase resolved, for example evanescent wave ellipsometry and evanescent wave spectroscopy (EWS, or Internal Reflection Spectroscopy), both of which may include evanescent field enhancement via surface plasmon resonance (SPR), Brewster angle refractometry, critical angle refractometry, frustrated total reflection (FTR), scattered total internal reflection (STIR) (which may include scatter enhancing labels), optical wave guide sensors; external reflection imaging, evanescent wave-based imaging such as critical angle resolved imaging, Brewster angle resolved imaging, SPR-angle resolved imaging, and the like. Further, photometric and imaging/microscopy methods, "per se" or combined with reflection methods, based on for example surface enhanced Raman spectroscopy (SERS), surface enhanced resonance Raman spectroscopy (SERRS), evanescent wave fluorescence (TIRF) and phosphorescence may be mentioned, as well as waveguide interferometers (e.g. Bio-Layer Interferometry as implemented by ForteBio®), waveguide leaky mode spectroscopy, reflective interference spectroscopy (RIfS), transmission interferometry, holographic spectroscopy, and atomic force microscopy (AFR).

Commercially available biosensors include the aforementioned BIACORE® system instruments, manufactured and marketed by GE Healthcare, which are based on surface plasmon resonance (SPR) and permit monitoring of surface binding interactions in real time between a bound ligand and an analyte of interest. In this context, "ligand" is a molecule that has a known or unknown affinity for a given analyte and includes any capturing or catching agent immobilized on the surface, whereas "analyte" includes any specific binding partner thereto.

While in the detailed description, the present invention is illustrated in the context of SPR spectroscopy, and more particularly the BIACORE® system, it is to be understood that the present invention is not limited to this detection method. Rather, any affinity-based detection method where an analyte binds to a ligand immobilised on a sensing surface may be employed, provided that a change at the sensing surface can be measured which is quantitatively indicative of binding of the analyte to the immobilised ligand thereon.

The phenomenon of SPR is well known, suffice it to say that SPR arises when light is reflected under certain conditions at the interface between two media of different refractive indices, and the interface is coated by a metal film, typically silver or gold. In the BIACORE® instruments, the media are the sample and the glass of a sensor chip, which is contacted with the sample by a micro fluidic flow system. The metal film is a thin layer of gold on the chip surface. SPR causes a reduction in the intensity of the reflected light at a specific angle of reflection. This angle of minimum reflected light intensity varies with the refractive index close to the surface on the side opposite from the reflected light, in the BIACORE® system the sample side.

Figure 1:
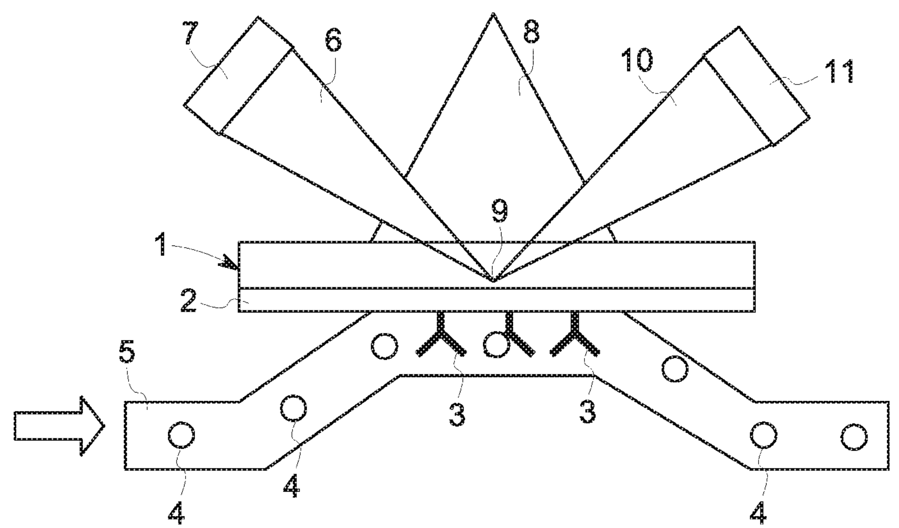
FIG. 1 is a schematic side view of a biosensor system based on SPR.

A schematic illustration of the BIACORE® system is shown in FIG. 1. Sensor chip 1 has a gold film 2 supporting capturing molecules (ligands) 3, e.g. antibodies, exposed to a sample flow with analytes 4, e.g. an antigen, through a flow channel 5. Monochromatic p-polarised light 6 from a light source 7 (LED) is coupled by a prism 8 to the glass/metal interface 9 where the light is totally reflected. The intensity of the reflected light beam 10 is detected by an optical detection unit 11 (photodetector array).

A detailed discussion of the technical aspects of the BIACORE® instruments and the phenomenon of SPR may be found in U.S. Pat. No. 5,313,264. More detailed information on matrix coatings for biosensor sensing surfaces is given in, for example, U.S. Pat. Nos. 5,242,828 and 5,436,161. In addition, a detailed discussion of the technical aspects of the biosensor chips used in connection with the BIACORE® instruments may be found in U.S. Pat. No. 5,492,840.

Figure 2:
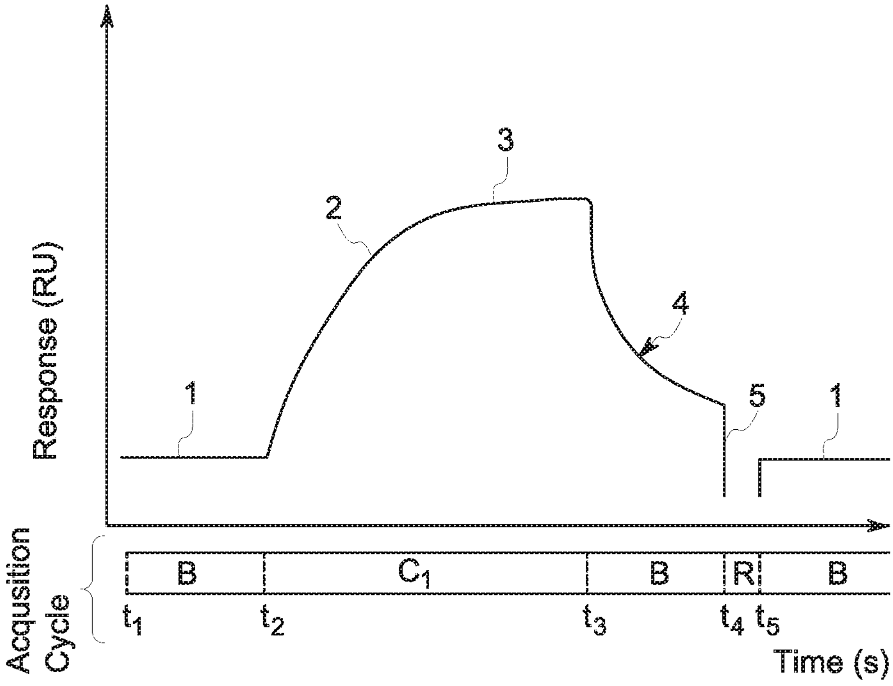
FIG. 2 is a representative sensorgram where the binding curve has visible association and dissociation phases.

When molecules in the sample bind to the capturing molecules on the sensor chip surface, the concentration, and therefore the refractive index at the surface changes and an SPR response is detected. Plotting the response against time during the course of an interaction will provide a quantitative measure of the progress of the interaction. Such a plot, or kinetic or curve (binding isotherm), is usually called binding curve or sensorgram, also sometimes referred to in the art as "affinity trace" or "affmogram". In the BIACORE® system, the SPR response values are expressed in resonance units (RU). One RU represents a change of 0.0001° in the angle of minimum reflected light intensity, which for most proteins and other bio molecules correspond to a change in concentration of about 1 pg/mm^ on the sensor surface. As sample containing an analyte contacts the sensor surface, the capturing molecule (ligand) bound to the sensor surface interacts with the analyte in a step referred to as "association." This step is indicated in the binding curve by an increase in RU as the sample is initially brought into contact with the sensor surface. Conversely, "dissociation" normally occurs when the sample flow is replaced by, for example, a buffer flow. This step is indicated in the binding curve by a drop in RU over time as analyte dissociates from the surface-bound ligand. A representative binding curve (sensorgram) for a reversible interaction at the sensor chip surface is presented in FIG. 2, the sensing surface having an immobilised capturing molecule, or ligand, for example an antibody, interacting with a binding partner therefore, or analyte, in a sample. The binding curves produced by biosensor systems based on other detection principles mentioned above will have a similar appearance. The vertical axis (y-axis) indicates the response (here in resonance units, RU) and the horizontal axis (x-axis) indicates the time (here in seconds). Below the horizontal axis, the acquisition cycle for acquiring a binding curve is schematically disclosed divided in different time sections where the sensor surface is put into contact with different fluids. Initially, from to t2, buffer (B) is passed over the sensing surface giving the baseline response I in the binding curve. Then, during from t2 to t3, the sensor surface is contacted with a sample containing an analyte at a concentration Ci whereby an increase in signal is observed due to binding of the analyte. This part II of the binding curve is usually referred to as the "association phase". Eventually, a steady state condition is reached at or near the end of the association phase where the resonance signal plateaus at III (this state may, however, not always be achieved). It is to be noted that herein the term "steady state" is used synonymously with the term "equilibrium" (in other contexts the term "equilibrium" may be reserved to describe the ideal interaction model, since in practice binding could be constant over time even if a system is not in equilibrium). At the end of the association phase, at t3, the sample is often replaced with a continuous flow of buffer (B) and a decrease in signal reflects the dissociation, or release, of analyte from the surface. This part IV of the binding curve is usually referred to as the "dissociation phase". The analysis is optionally ended by a regeneration step, at t4, where a solution capable of removing bound analyte from the surface (R), while (ideally) maintaining the activity of the ligand, is injected over the sensor surface. This is indicated in part V of the sensorgram. At is injection of buffer (B) restores the baseline I and the surface is now ready for a new analysis. In some situations it may be convenient to omit the regeneration step V and initiate a new injection cycle without regeneration. Examples of such situations comprise concentration series of the same analyte, screening of analytes with a sufficiently high dissociation rate to allow essentially complete dissociation, etc.

A plurality of injections may be performed sequentially in one and the same experimental cycle without intermediate regeneration or renewal of the immobilized ligand, and is described in more detail in US 2013/0065251 A1. An example is also shown in FIG. 3, where a plurality of fluid samples containing analyte at different concentrations are injected without regeneration.

From the profiles of the association and dissociation phases II and IV, respectively, information regarding the binding and dissociation kinetics is obtained, and the height of the binding curve at III represents affinity (the response resulting from an interaction being related to the change in mass concentration on the surface).

Using some biosensor systems, such as the BIACORE® 4000 for instance, a plurality of independent flow cells, each containing a plurality of detection spots, are arranged to perform multiple analyses simultaneously. Each flow cell has its own needle, enabling parallel injections to each flow cell and allowing for the combination of a plurality of ligands each with their own analytes or indeed of one ligand with multiple samples containing varying concentrations of analyte. This type of analysis is generally referred to as parallel analysis.

As mentioned the present invention relates to a method and a biosensor system for evaluation of an interaction between an analyte in a fluid sample and a ligand immobilized on a sensor surface of a biosensor. The biosensor may be based on any type of interaction-based detection method where an analyte binds to a ligand immobilized on a sensing surface, provided that a change at the sensing surface can be measured which is quantitatively indicative of binding of the analyte to the immobilized ligand thereon.

FIG. 4 discloses steps of the method for evaluation of an interaction between an analyte in a fluid sample and a ligand immobilized on a sensor surface of a biosensor according to a preferred embodiment of the present invention. In a first step 101, a plurality of fluid samples, each containing known concentrations of analyte, are provided. The fluid samples may be based on a fluid containing a given concentration of an analyte that is divided into smaller samples and diluted according to a predetermined dilution schedule, as will be further described below.

In a second step 102, a plurality of needles and a plurality of sensor surfaces or detection spots are provided, at least some of the sensor surfaces or detection spots having a known amount of ligand immobilized thereon, and each needle being configured to inject a fluid sample to a sensor surface or detection spots. In this preferred embodiment a biosensor system with a plurality of flow cells arranged in parallel is used to enable simultaneous analysis of a large number of fluid samples. In another embodiment, it would be possible to use a biosensor system with only one sensor surface but multiple detection spots on said sensor surface.

In a third step 103, the plurality of fluid samples are divided into at least two groups, each group having a number of fluid samples corresponding to the number of needles. The fluid samples may be arranged in wells on a plate as shown by FIG. 5 so that the samples of one group are distributed along a horizontal axis in the figure. The number of samples in a group is thus selected to correspond to the number of needles of the biosensor system to allow every fluid sample of the group to be injected simultaneously.

In a fourth step 104, the fluid samples of a first of said groups are injected to the sensor surfaces or detection spots by means of the needles to permit association of the analyte to the ligand, and in a fifth step each sensor surface or detection spot is monitored and binding data is collected. After the fluid samples containing analyte has been injected, buffer solution is added to prepare the sensor surface for the next injection of analyte but no regeneration is performed.

The steps of injecting the fluid samples, monitoring the interaction at each sensor surface or detection spot and collecting binding data are repeated for each subsequent group of fluid samples until all samples have been used. In order to facilitate this, the fluid samples of each group may be arranged in a row on a plate comprising a plurality of wells arranged in columns and rows. When another group is to be used, the needles of the biosensor system and the plate may be arranged to move in relation to each other so that the needles are positioned above the wells containing fluid samples of the next group.

The binding data for the interaction at each sensor surface or detection spot may be combined to form a binding curve, displaying all fluid samples injected to that particular surface or spot. For a system having eight needles, the result of the experiment would then be eight graphs or curves, as shown by FIG. 5 and described below, and from these binding curves the kinetic parameters can be determined.

It is especially advantageous that the steps of the method are performed without regeneration of the sensor surfaces holding the ligand or renewal of the ligand itself, since this allows for a single cycle process with significantly shortened time for the analyses compared to a multi cycle process having regeneration between each injection of fluid sample containing analyte. In some embodiments, one or more of the sensor surfaces or detection spots may be free from ligand and provide a reference.

After all fluid samples have been used, the sample binding curves acquired may be stored, analyzed and/or displayed, allowing a user of the system an overview of the interaction between ligand and analyte at different concentrations. The sample binding curves are preferably also stored in a computer readable medium. The term computer readable medium as used herein is to be understood as any medium suitable for storing data for access by a computer or similar tool, such as an RAM, a memory stick, a compact disc, etc. When displaying the sample binding curves, it is advantageous to show all curves in one graph, to allow the user to compare the shape of the curves and remove those deemed to be of low quality or out of concentration scope for the interaction.

FIG. 5 discloses a plurality of needles 19 placed above a plate 12 having a plurality of wells 13 arranged in rows so that the needles 19 have access to a first row 14. The dilution series of analyte containing fluid samples may be distributed according to a predetermined pattern with the fluid sample having the highest concentration at one end 17 of the first row 14 and decreasing concentrations being distributed along the row. Similarly, in the next row 15 the fluid sample having the highest concentration may be located at one end 17 and the lowest concentration or indeed a blank sample containing no analyte at all at another end 18. In this way a dilution series can be created simply and efficiently. During the fourth and fifth steps 104, 105 of the method according to the present invention, the fluid samples of each group or row 14, 15, 16 are removed from the wells by use of the needles 19 and injected to the sensor surface or surfaces, to acquire the sample binding curves displaying the interaction between analyte and ligand.

The sample binding curves from the interaction between the ligand on the sensor surface or surfaces and the analyte in the fluid samples are shown in a graph 20 in FIG. 5. Here, the binding data collected at each sensor surface or detection spot has been combined to form binding curves. It is advantageous if the fluid samples injected progress from a low towards a higher concentration of analyte. The biosensor system shown has eight needles, allowing for eight fluid samples in the first group or row 14, and each needle thus moves along one column having one well for each row 14, 15, 16. The resulting graphs from the interaction between ligand and analyte in the fluid samples of one row are disclosed in FIG. 5 with numerals 21, 22, 23, 24, 25, 26, 27, 28. Depending on the concentration of analyte in each fluid sample, the resulting graph may show too small or too large sensor response, and the aim of the user is consequently to identify the graphs that are suitable for further analysis to yield information regarding the kinetic properties of the interaction between ligand and analyte.

In FIG. 5, a first graph 21 shows interaction between ligand and blank samples, without analyte, giving an essentially horizontal line to allow for reference subtraction to improve the results. A second and third graph 22, 23 show too small response to be of use, while a fourth, fifth and sixth graph 24, 25, 26 show curves suitable for analysis. A seventh graph 27 has a sensor response that approaches the limit of being too high to be suitable for analysis. An eighth graph 28, finally, has too large sensor response to be suitable for analysis. For a user confronted with these graphs, all but three may be removed so that only those showing the best results are left and can be displayed together in a global graph 20. It is to be noted that this determination of the graphs suitable for further analysis can be performed by a user or by software that uses some exclusion criteria to determine which responses fit with the expected results. Criteria for determining the quality of a sensorgram may be total response or a predetermined value for the increase in response over the entire curve, among others.

After removal of the unsuitable graphs the remaining curves thus allows for subsequent analysis to determine kinetic parameters such as association rate constant, dissociation rate constants that describe the interaction between ligand and analyte in more detail. Depending on the concentration of analyte used in the fluid samples of the columns giving the satisfactory binding curves it is also possible to determine more closely the concentration range suitable for studying the interaction. Thus, rather than experimenting or performing cumbersome calculations to establish the concentration range in question one single cycle of experiments can be performed to yield the desired information in a shorter time and less effort than previously possible.

FIG. 6 shows one example of a dilution series for the fluid samples containing analyte that is suitable for use with the method and system of the present invention. Each column corresponds to one needle (numbered 1-8) and the dilution factor is given for each well on a plate having three rows. For one needle a blank series is used and for the other needles a dilution factor of five for each step along a row and a dilution factor of two along each column are used to provide a wide range of concentrations. Thanks to the wide range used the probability is high that satisfactory results are obtained from just one experiment, compared to the chances using previous methods where a smaller concentration range is generally established and a dilution series of only a few samples are used.

FIG. 7 shows another embodiment of the invention where the immobilization level of the ligand is varied on the sensor plates of the biosensor corresponding to each needle or column. Thereby, steric effects and mass transport properties can be determined and handled, among others. It is advantageous to select the lowest levels of immobilized ligand to correspond to the highest concentration of analyte, to increase the chances of producing binding curves with sufficient response levels to yield satisfactory graphs. By using this embodiment, preferably in combination with the preferred embodiment described above, the suitable immobilization levels can be determined without pre-evaluation or cumbersome calculations, in a manner similar to the suitable concentration interval for the analyte.

The word needle(s) used herein is not intended to be unduly limiting. Herein 'needle' is intended to mean a hollow element forming a fluid path preferably of a size similar to that used as a hypodermic syringe e.g. having a fluid path of 0.8 mm squared (1 mm diameter) or less, but not necessarily that size. Any hollow member which has a fluid path having a terminal end small enough to hold fluids in place under surface tension will suffice as a 'needle' for this invention.

The invention is not to be seen as limited by the embodiments described above but can be varied within the scope of the appended claims, as will be readily understood by the person skilled in the art. For instance, the number of needles and channels can be varied, detection spots or flow cells can be used, inter flow cell referencing configuration can be used, one blank detection spot for each needle may be used, the plate format may be varied, different dilution factors and concentration levels can be used, and random concentration variations or other concentrations than a dilution series can be used.

The invention claimed is:

1. A method for evaluating an interaction between an analyte and an immobilized ligand in a biosensor, comprising the steps of providing a plurality of fluid samples, each containing known concentrations of analyte;

providing a plurality of sensor surfaces or detection spots, at least some of the sensor surfaces or detection spots having a known amount of ligand immobilized thereon;

dividing said plurality of fluid samples into at least two groups, each group having a number of fluid samples corresponding to the number of fluid samples;

injecting the fluid samples of a first of said groups via a plurality of needles to the sensor surfaces or detection spots to permit association of the analyte to the ligand;

monitoring the plurality of sensor surfaces or detection spots to collect binding curve data for each monitored group; and repeating the steps of injecting fluid samples and monitoring the sensor surfaces or detection spots and collecting binding curve data for each group of fluid samples, wherein the steps above are performed without intermediate regeneration or renewal of the immobilized ligand, wherein the needles arranged in parallel to simultaneously inject different concentrations of analyte into onto the plurality of sensor surfaces or detection spots in accordance with a first parallel concentration series, and each group of sensor surfaces or detection spots is injected with analyte sequentially by the needles arranged in parallel according to a second sequential concentration series.

2. A method according to claim 1, wherein the plurality of fluid samples form a dilution series where each sample has a concentration of analyte that differs from all other samples.

3. A method according to claim 1, wherein the binding data collected at each sensor surface or detection spot is stored and/or displayed together as a binding curve.

4. A method according to claim 3, wherein a quality of a binding curve is determined based on total response or a predetermined value for the increase in response over the entire curve.

5. A method according to claim 3, wherein some sample binding curves can be removed so that remaining sample binding curves can be displayed together.

6. A method according to claim 1, wherein the amount of ligand immobilized on one sensor surfaces or detection spot differs from the amount of ligand immobilized on another sensor surface or detection spot.

7. The method according to claim 1, wherein the binding curve data for each group comprises a measured resonance unit (RU) over time.

8. The method according to claim 1, wherein the first parallel concentration series is according to a first dilution factor, and the second sequential concentration series is according to a second dilution factor, the first dilution factor being greater than the second dilution factor.

9. The method according to claim 8, wherein the first dilution factor is 5× and the second dilution factor is 2×.

* * * * *